United States Patent
Marszalek

(10) Patent No.: US 6,509,745 B1
(45) Date of Patent: Jan. 21, 2003

(54) METHOD AND APPARATUS FOR MEASURING LIQUID DIELECTRIC BEHAVIOR

(75) Inventor: Gary A. Marszalek, South Lyon, MI (US)

(73) Assignee: Detroit Diesel Corporation, Detroit, MI (US)

(*) Notice: Subject to any disclaimer, the term of this patent is extended or adjusted under 35 U.S.C. 154(b) by 77 days.

(21) Appl. No.: 09/669,162

(22) Filed: Sep. 25, 2000

(51) Int. Cl.[7] ............................................. G01R 27/26
(52) U.S. Cl. ........................ 324/663; 324/658; 324/698
(58) Field of Search ................................. 324/658, 664, 324/663, 665, 668, 670, 676, 677, 678, 698

(56) References Cited

U.S. PATENT DOCUMENTS

| | | | |
|---|---|---|---|
| 4,429,272 A | * 1/1984 | Bungay | ........................ 324/61 |
| 4,459,541 A | 7/1984 | Fielden et al. | |
| 4,736,156 A | * 4/1988 | Benson et al. | ................ 324/61 |
| 4,743,837 A | 5/1988 | Herzog | |
| 5,073,757 A | * 12/1991 | George | ........................ 324/677 |
| 5,262,732 A | * 11/1993 | Dickert et al. | ............... 324/672 |
| 5,283,528 A | 2/1994 | van Seeters | |
| 5,586,042 A | * 12/1996 | Pisau et al. | ................ 364/482 |
| 5,604,441 A | * 2/1997 | Freese et al. | ................ 324/663 |
| 6,028,433 A | 2/2000 | Cheiky-Zelina et al. | |
| 6,194,903 B1 | 2/2001 | Schulz | |

* cited by examiner

Primary Examiner—Christine Oda
Assistant Examiner—Amy He
(74) Attorney, Agent, or Firm—Brooks & Kushman P.C.

(57) ABSTRACT

A system and a method for measuring capacitance of a capacitor having a dielectric material, such as a lubricating oil, disposed between the electrodes of the capacitor, where the dielectric material causes a double layer effect within the capacitor. A variable source is provided in series with a resistor to induce a change in a current flowing through the capacitor. A sensor converts the resulting current flow into a current value readable by a processor. The processor records a plurality of current values. An initial value is recorded to correspond to the induced change in the current. A leakage value is recorded after the current has exponentially decayed to approximate steady state. Multiple other current values are also recorded during the exponential decay. An intermediate value is then selected from among the multiple other current values based upon the initial value and the leakage value. The capacitance of the capacitor is then calculated based upon the initial value, intermediate value, leakage value and a resistance of the series resistor.

18 Claims, 3 Drawing Sheets

METHOD AND APPARATUS FOR MEASURING LIQUID DIELECTRIC BEHAVIOR

TECHNICAL FIELD

The present invention relates to a capacitor based method of measuring dielectric characteristics of a liquid disposed between the electrodes of the capacitor.

BACKGROUND ART

Capacitance based sensors are commonly used to measure the quality of lubricating oils and other fluids used in engines and machinery. The capacitor sensors are positioned so that the fluid flows between the electrodes. A dielectric value of the fluid changes as the quality of the fluid degrades over time, temperature, use, and an introduction of other fluid types. For example, the dielectric value of engine lubricating oil tends to increase over time due to use, and will increase immediately if breached by water or glycol. This changing dielectric value results in a measurable change in the total capacitance of the capacitor sensor. When the dielectric value reaches a predetermined threshold then it is time to perform maintenance and replace the fluid.

Electric circuits used to measure the total capacitance of the capacitor sensor often operate by measuring a time required to charge/discharge the capacitor to/from a predetermined voltage threshold using a known voltage and a known series resistance. This method of measuring capacitance assumes that the fluid's dielectric behavior is static. In other words, that the fluid behaves similar to a solid dielectric.

Lubricating oils and similar fluids often have different dielectric behavior than solid dielectric materials. Fluids often contain contaminants that exhibit dipole moments and electrostatic charges. These contaminants will move when exposed to the electric field created between charging electrodes within the capacitor. Dipole contaminants in homogeneous electric fields will move until they align with the field and the forces acting upon the two separate charges of the dipole cancel each other. Dipole contaminants in inhomogeneous electric field will experience electrostriction where the dipole contaminants are forced in a direction toward increasing field strength thus causing an elastic deformation of the fluid.

Ionized contaminants will move under the influence of homogeneous and inhomogeneous electric fields. Positively charged contaminants will move toward the negatively charged electrode, and negatively charged contaminants will move toward the positively charged electrode. The net result is a double-layer effect within the capacitor as the charged contaminants accumulate at the surface of the electrodes. Speed of the contaminant movement depends upon the electric field's amplitude and rate of change, as well as the viscosity of the fluid through which the contaminants must move.

Dynamic contamination movement results in a time-dependent capacitance of the capacitor sensor. Conventional measuring techniques will result in varying capacitances depending upon the charge rate and predetermined voltage threshold used in the measurement. Short charge times do not give the contaminants sufficient time to reach equilibrium. Consequently, the measured capacitance is subject to random fluctuations as the contaminants move about between the electrodes. Long charge times allow the contaminants to stabilize. However, as the capacitor becomes fully charged, minor variations in the predetermined voltage can result in large changes in the measured charging time and thus the measured capacitance.

Not all contaminants will cause a change in the dielectric value. In some cases, the contaminant is another type of fluid having approximately the same dielectric value. For example, adding diesel fuel to clean engine lubricating oil causes little change in the measured dielectric constant. The quality of the fluid may be degraded by another fluid and yet conventional dielectric sensing techniques will not detect the degradation. The end result is that conventional capacitance based sensor measurements techniques lack accuracy under common conditions.

DISCLOSURE OF INVENTION

The present invention is a system and a method for measuring capacitance of a capacitor having a dielectric material disposed between the electrodes of the capacitor. The present invention utilizes a variable source in series with a resistor to induce a change in a current flowing through the capacitor. A sensor converts the resulting current flow into a current value readable by a processor. The processor records a plurality of current values at a plurality of times. An initial value is recorded corresponding to the induced change in the current. A leakage value is recorded after the current has exponentially decayed to approximate steady state. Multiple other current values are also recorded during the exponential decay.

An intermediate value is selected from among the multiple other current values based upon the initial value and the leakage value. The initial value, leakage value, intermediate value, a time between inducing the change in the current and determining the intermediate value, and a resistance of the resistor are then used to calculate the capacitance. This approach works well when the dielectric material causes a double-layer effect in the capacitor. This is because the capacitor is allowed to become almost fully charged and thus the electric field and the dielectric material within the electric field are given time to become stable.

In the preferred embodiment, the intermediate value is selected to be approximately equal to an ideal value set at 20 percent of the difference between the initial value and the leakage value. This places the intermediate value at a point on the exponential current decay where the capacitor has achieved a majority of its full charge and the measured current is changing at a moderate rate allowing for good analog to digital conversion. In alternative embodiments, the intermediate value is selected from a range of interest around the ideal value.

Once the capacitance has been calculated, a dielectric value for the fluid can be calculated from the capacitance and a known geometry of the capacitor sensor. The dielectric value provides a good trending indicator of the contamination levels within the fluid. Furthermore, a dielectric dissipation factor may also be calculated.

A conductivity of the dielectric material may also be calculated based upon the geometry of the capacitor, an applied voltage and the measured leakage value. This information is useful in trending changes to the dielectric material that do and do not cause a change in the dielectric value of the fluid.

A viscosity ratio of a fluid dielectric may be determined by measuring the leakage values at approximately 40 and 100 degrees Celsius and then calculating their ratio.

Accordingly, it is an object of the present invention to provide a system and method for measuring a capacitance of a capacitor having a dielectric disposed material between the electrodes of the capacitor where the dielectric creates a double-layer effect between the electrodes.

These and other objects, features and advantages will be readily apparent upon consideration of the following detailed description in conjunction with the accompanying drawings.

BEST MODE FOR CARRYING OUT THE INVENTION

Figure 1:
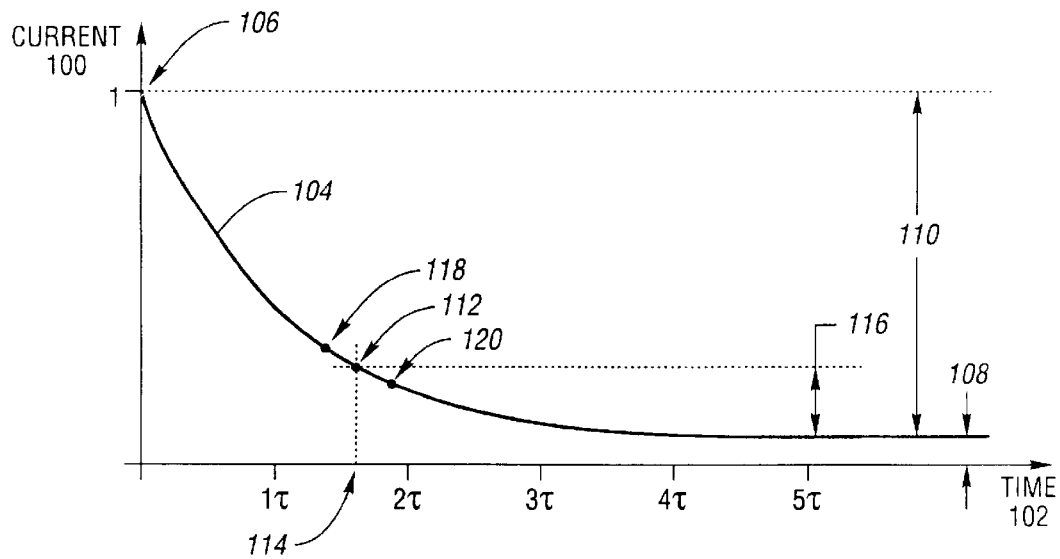
FIG. 1 is a graph of a current flowing through a capacitor as a function of time.

FIG. 1 is a normalized graph of a current 100 flowing through a capacitor being charged by a voltage in series with a resistor. A time 102 dependent value of the current 100 is shown as line 104. Current value 104 starts at an initial value 106 at time zero. Here, the initial value 106 is normalized to unity. Current value 104 then undergoes an exponential decay as time 102 increases and the capacitor approaches a full charge. A rate of decay is determined by a time constant τ (tau) which is a product of a capacitance of the capacitor and a resistance of the series resistor. If the capacitor is an ideal capacitor, then the current value 104 would approach zero amperes at large values of time 102. In practical applications, a large value of time is anything greater than approximately five time constants (5τ). Real capacitors also exhibit a leakage current, shown a leakage value 108, that appears as a constant for large values of time.

The exponential decay of the current 100 flowing through the capacitor can be modeled by equation 1 as:

$$I(t) = I_p e^{(-t/RC)} + I_L \quad (1)$$

where $I_p$ is a peak value 110, $I_L$ is the leakage value 108, R is the resistance of the series resistor, and C is a capacitance of the capacitor. Leakage value 108 can be determined by measuring the current 100 at or after approximately five time constants after time zero. Since the actual value of the capacitance C is still unknown at this point, it may be approximated with a predetermined capacitance value for the purpose of determining when five time constants have elapsed. Peak value 110 can be determined by calculating a difference between the initial value 106 and the leakage value 108.

A third or intermediate value 112 must be determined in order to calculate the capacitance C. Preferably, the intermediate value 112 should be determined in a range of time 100 between the first time constant (1τ) and the fourth time constant (4τ). Determining the intermediate value 112 prior to the first time constant (1τ) may result in an inaccurate measurement as it is difficult to sample the rapidly changing current value 104. A small jitter in time 102 while measuring the current results in a large difference in current value 104. Furthermore, the capacitor has not been given much time to charge thus the dynamic characteristics of the dielectric material will have a large impact on the actual value measured. Likewise, determining the intermediate value after the fourth time constant (4τ) may also result in an inaccurate measurement. Current value 104 changes very little for modest changes in time 102 beyond the fourth time constant 4τ. Consequently, the actual change in the current value 104 over time 102 may be hidden due to noise associated with the measurement.

Normalizing the graph in FIG. 1 so that the initial value 106 represents unity for the current 100, and the fifth time constant (5τ) represents unity for time 102, then the ideal time to determine the intermediate value 112 is at approximately 1.609 time constants, as indicated by time 114. A tangent line (not shown) to the current value 104 has a slope of minus one at time 1.609τ. In other words, a charge angle for the capacitor is 45 degrees=arctan (slope) at time 1.609τ (ideal time 114). At ideal time 114, small errors in time 102 result in similar small errors in the measured current value 104. Furthermore, stepping from one moment in time 102 to the next moment results in a modest and measurable change in the current value 104. Still further, the current 100 has decreased to only 20 percent of the peak value 110, as indicated by distance 116, so the capacitor is approaching a fully charged condition. In this case, intermediate value 112 is selected to be the closest current value to an ideal value equal to 20 percent of the peak value 110.

In an alternative embodiment, it is not necessary to determine the intermediate value 112 at the ideal time 114. Instead, intermediate value 112 may be selected from a range of interest around the ideal time 114. The range of interest may span, for example ±5 percent, ±10 percent, or ±20 percent of the ideal time 114. As shown in FIG. 1, an example range of interest extends from 28 percent of the peak value 110, as indicated by point 118, to 15 percent of the peak value 110, as indicated by point 120. Expressed in terms of time 102, the range of interest spans between 80 percent of the ideal time 114 to 120 percent of the ideal time 114. Current value 104 may be determined with a reasonable degree of accuracy anywhere within this region of interest.

Once the intermediate value 112 has been determined, and the time at which the intermediate value 112 was determined is known, then the only unknown left in equation 1 is the capacitance C. Solving for capacitance C produces equation 2 as follows:

$$C = -t/(R \ln((I(t)-I_L)/I_p)) \quad (2)$$

Figure 2:
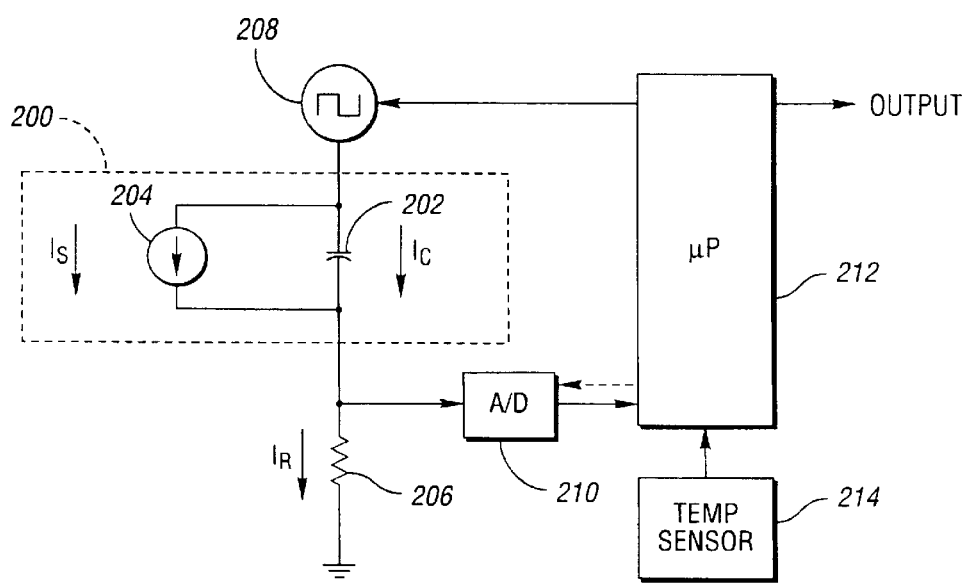
FIG. 2 is a block diagram of a circuit for measuring a dielectric value.

FIG. 2 is an example of a system that implements the method of the present invention. The capacitor sensor 200 is modeled as an pure capacitor 202 with a dielectric material (not shown) having a dielectric value of k. A solution current $I_S$ is modeled as a constant current source 204 parallel to the capacitance 202 having the leakage value 108 ($I_L$). Resistor 206 has a value of R and is connected in series with the capacitor 202. A variable voltage source 208 is used to induce a change in the reactive current $I_C$ flowing through the capacitor 202. Resistor current $I_R$ flowing through resistor 206 is the sum of the reactive current $I_C$ and the solution current $I_S$.

An analog to digital converter 210 converts a voltage produced across the resistor 206 into a voltage value. Current value 104 is proportional to the voltage value and inversely proportional to the known resistance R of resistor 206 (i.e., I=V/R). Analog to digital converter 210 may be free-running, or it may receive a triggering signal (shown in phantom) from a microprocessor 212.

Microprocessor 212 receives the voltage values from the analog to digital converter 210 as an input and outputs a timing signal to the variable voltage source 208. The timing signal inform s the variable source generator 208 when to transition its output voltage. Microprocessor 212 may also receive a temperature signal from a temperature sensor 214 representative of a temperature of the dielectric material between the electrodes of the capacitor 202. Temperature information will be used later when calculating a viscosity ratio for the dielectric material.

In an alternative embodiment, the analog to digital converter 210 may be replaced by a current sensor (not shown) in series with resistor 206. This current sensor would measure the resistor current $I_R$ directly in units of amperes. In this case the microprocessor 212 would be free from the task of converting the resistor voltage values into resistor current values. Other variations are also possible within the scope of the present invention including, but not limited to employing a variable current source (not shown) in place of the variable voltage source 208.

Figure 3:
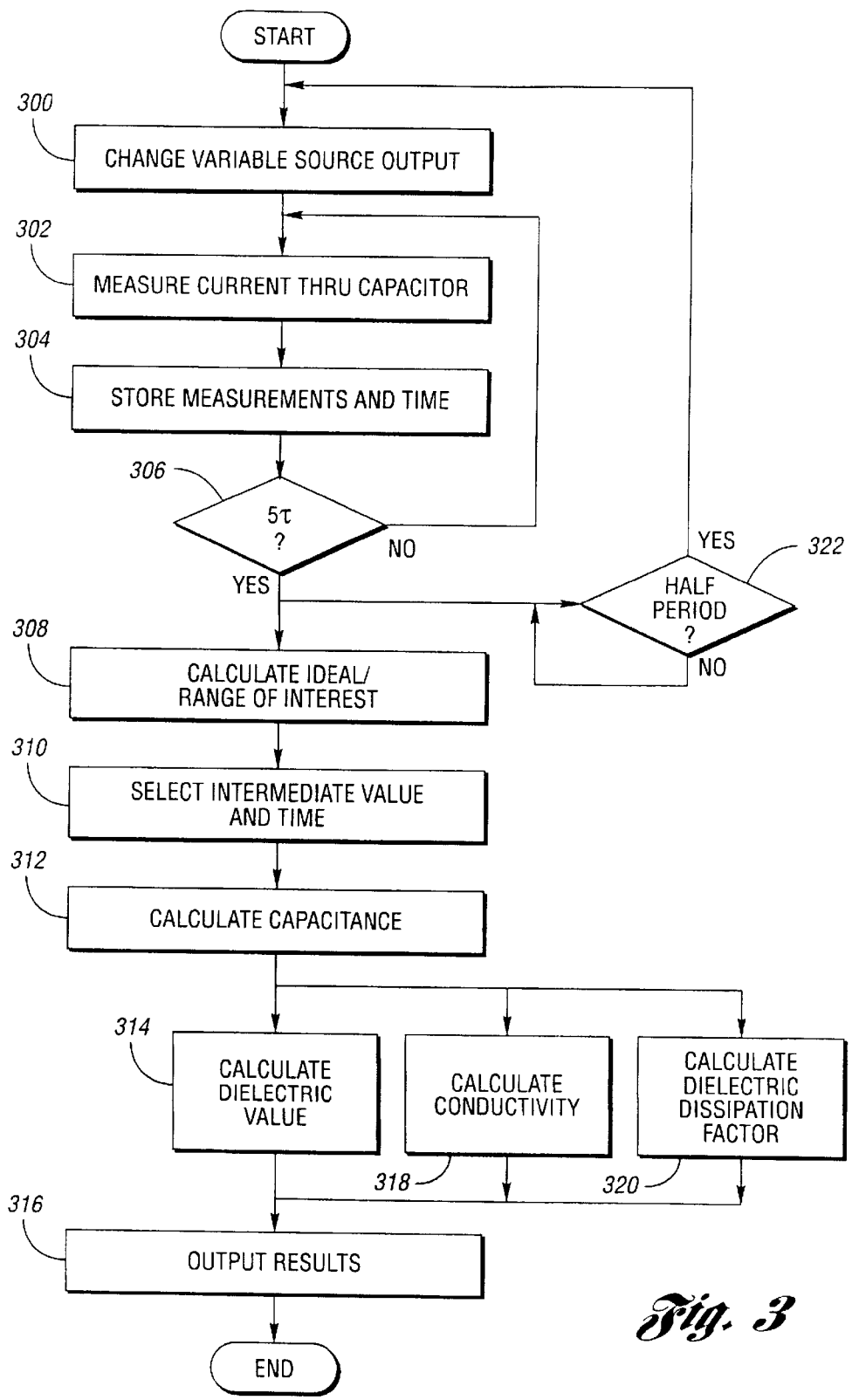
FIG. 3 is a flow diagram of a method for measuring the dielectric value.

FIG. 3 is a flow diagram showing the operation of the system of FIG. 2. Operations start by changing the variable voltage source's output, as shown in block 300. The change is typically a step function between a negative peak voltage and a positive peak voltage. A step from zero volts to a peak voltage may also be used. Changing the variable voltage source's output causes the reactive current $I_C$ flowing through capacitor 202 to change. This change in current is measured by measuring the voltage across the resistor 206, as shown in block 302. Each current value 104, as determined by measuring the voltage across the resistor 206, and a time value at which the respective current value 104 was determined are then stored by the microprocessor 212, as shown in block 304.

Additional current values 104 and time values are stored by the microprocessor 212 for up to five time constants after the change in the variable voltage source's output, as shown by the NO branch of decision block 306. After five time constants have passed, no additional current values 104 and time values need to be recorded, as shown by the YES branch of decision block 306, although they could.

Microprocessor 212 then calculates an ideal current value, or the range of interest for the current values 104 in some applications, shown in block 308. The intermediate value is then selected from among the multiple current values 104 stored earlier, as shown in block 310. If the ideal current value approach is used, then the intermediate value is selected as the closest value to the ideal value. Where the range of interest approach is used, then the intermediate value is selected to be anywhere within the range of interest.

Using the intermediate value, the time at which the intermediate value was determined, the initial value recorded at time zero, the leakage value recorded at or after five time constants, and the known value R of the resistor 206, microprocessor 212 calculates the capacitance C of the capacitor sensor 200, as shown in block 312.

Given that a geometry of the capacitor sensor 200 is known to the microprocessor 212, then the microprocessor 212 can calculate the dielectric value of the dielectric material, as shown in block 314. The dielectric value, and optionally the leakage value, are finally output by the microprocessor 212, as shown in block 316. Where the capacitor sensor 200 has a parallel plate configuration, then the capacitance C is defined by equation 3 as;

$$C = A\varepsilon_0 k/d \quad (3)$$

where A is the area of one plate, $\varepsilon_0$ is the permittivity of a vacuum, k is the dielectric value for the dielectric material, and d is the distance between the parallel plates. Where the capacitor sensor 200 has a coaxial cylindrical configuration then, the capacitance C is defined by equation 4 as:

$$C = 2\pi h \varepsilon_0 k/\ln(A/B) \quad (4)$$

where h is the height of the cylinder, A is the outside diameter of the inner cylinder, and B is the inside diameter of the outer cylinder.

When the dielectric material is a lubricating oil in a machine or engine environment, then the oil's dielectric value is sensitive to soot contamination. Higher levels of soot contamination result in higher dielectric values. One can determine when the oil has reached the end of its useful life by trending changes in the oil's dielectric value. When the dielectric value reaches a predetermined threshold then it is time to replace the oil.

The dielectric value of the lubricating oil is also sensitive to intrusions by water and glycol-based coolants. By monitoring the dielectric value, one can determine quickly when the lubricating oil has become contaminated with water or glycol. A sudden change in the dielectric value typically indicates that a failure has occurred in an internal seal and that maintenance should be performed immediately.

Microprocessor 212 may output the leakage value 108 as representative of a base conductivity of the lubricating oil. The leakage value 108 is sensitive to oxidation and changes in the total base number for the oil as well as the viscosity of the oil. In addition, rapid changes in the leakage value 108 may indicate an intrusion of water, glycol, or diesel fuel into the oil. In an alternative embodiment, a conductivity of the fluid may also be calculated, as shown in block 318. The conductivity is based upon the geometry of the capacitor sensor 200, the measured leakage value 108 and the strength of the electric field applied across the fluid.

Microprocessor 212 may also use knowledge of the leakage current and the peak current to calculate a dielectric dissipation factor, as shown in block 320. Dielectric dissipation factor is defined as shown in equation 5:

$$\tan(\delta) = \text{reactive current/solution current} = I_P/I_L \quad (5)$$

The dielectric dissipation factor is approximately 90 degrees when there is little to no solution current $I_S$, and a smaller angle when contaminants such as soot, oxidation and total base number variations cause larger solution currents $I_S$. Trending the dielectric dissipation factor is another indicator of the level of contamination within the lubricating oil.

Microprocessor 212 may repeat the process shown in FIG. 3 twice each period, the YES branch of decision block 322. By reversing the polarity on the variable voltage source output, the capacitor sensor 200 can be charged to the opposite polarity through resistor 206 during the second half of the period. During this charging, the voltage across resistor 206 can be measured and updated values for the dielectric value and dielectric dissipation factor can be calculated. Since the measurements of the resistor voltage must take place over at least five time constants, then the variable voltage source's output must have a period greater than or equal to ten time constants for two measurements per period.

Figure 4:
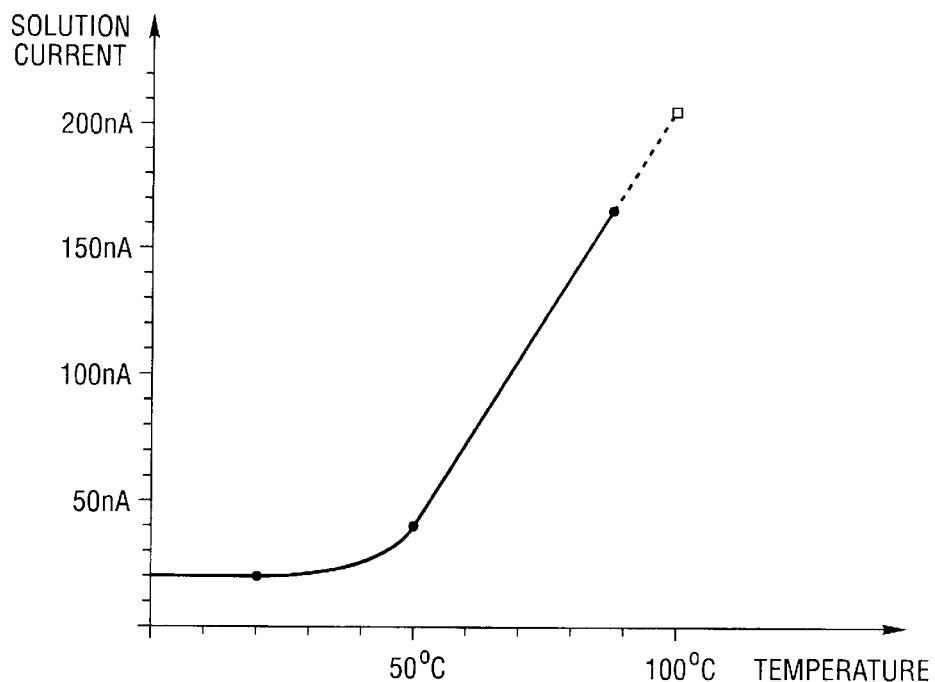
FIG. 4 is a graph of a solution current flowing through a lubricating oil as a function of temperature.

As mentioned above, the solution current $I_S$ is sensitive to the viscosity of the lubricating oil. Experimental results of solution current as a function of temperature of a 4.06 percent soot loaded oil is shown in FIG. 4. The experiment showed that a ratio of the solution current value (leakage value) at 100 degrees Celsius to the solution current value at 40 degrees C matches the viscosity ratio of the oil sample. In particular, the ratio of solution currents (predicted 204 nanoamperes/27 nanoampers=7.56) correlates very well to the ratio of viscosity at 40 degrees to 100 degrees (124.1 centistokes to 16.4 centistokes=7.57).

Determining the viscosity ratio of a lubricating oil allows for trends within a brand of oil to be monitored, as well as changes to a different brand of oil. Another helpful feature is that the calculated viscosity ratio can also be used to detect intrusions of other fluids that have similar dielectric values as the lubricating oil. In particular, the dielectric value of diesel fuel is similar to that of engine oil. When a seal failure or other problem results in diesel fuel spilling into the engine oil, then the dielectric measurements may not detect the problem. The viscosity ratio measurement, on the other hand, will signal a change by decreasing in response to the presence of the diesel fuel.

Figure 5:
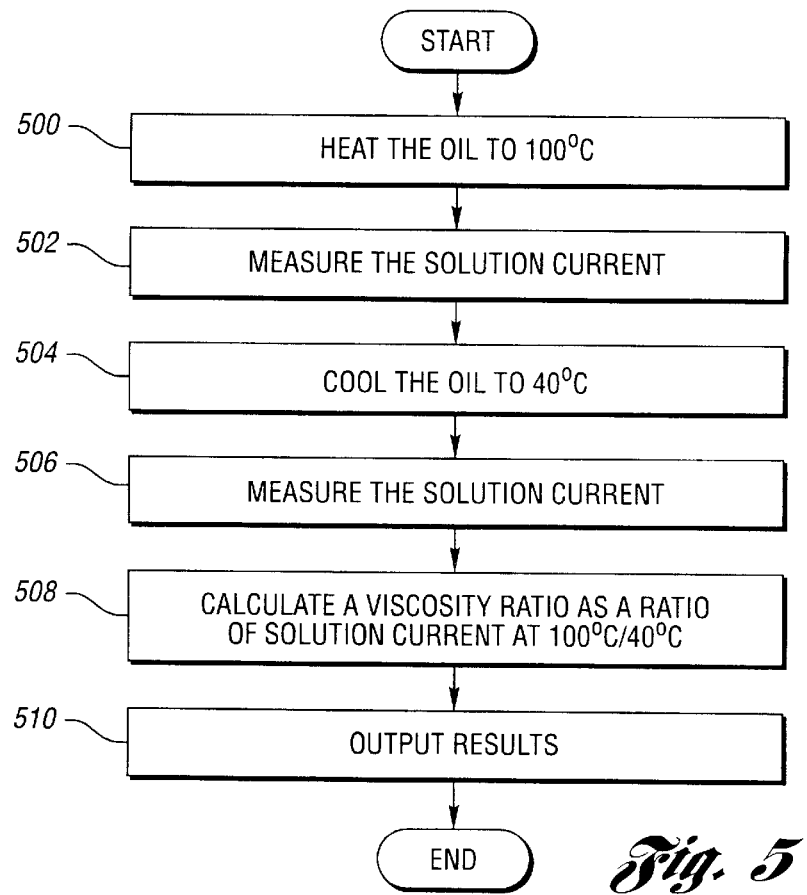
FIG. 5. is a flow diagram of a method for determining a viscosity ratio.

FIG. 5 is a flow diagram of a method for determining the viscosity ratio based upon the solution current. The lubricating oil must first be heated to approximately 100 degrees Celsius, as shown in block 500. This is commonly accomplished by operating the engine and allowing its own internal heat to warm the oil. The solution current $I_S$ is measured when the oil is at 100 degrees Celsius, as shown in block 502 and the resulting leakage value stored. Measurement of the solution current may be accomplished the same as shown in FIG. 3. During a subsequent cooldown, the lubricating oil cools eventually reaching approximately 40 degrees Celsius, as shown in block 504. Once again, the solution current $I_S$ is measured to produce a second leakage value, as shown in block 506. The ratio of the leakage value at 100 degrees Celsius to the leakage value at 40 degrees Celsius is then calculated, as shown in block 508, to produce the viscosity ratio. Finally, the viscosity ratio is output, as shown in block 510.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for measuring a capacitance of a capacitor, the method comprising:

inducing a change in a current flowing through the capacitor;

determining a plurality of current values in response to inducing the change in the current flowing through the capacitor, the plurality of current values including an initial value and a leakage value determined while the current is approximately steady state;

selecting an intermediate value from the plurality of current values in response to determining the plurality of current values; and calculating the capacitance of the capacitor based upon the initial value, the leakage value, the intermediate value, and a time between inducing the change in the current flowing through the resistor and determining the intermediate value in response to selecting the intermediate value.

2. The method of claim 1 further comprising:

delaying at least five time constants after inducing the change in the current flowing through the capacitor to determine the leakage current, where one time constant is defined as a product of a predetermined capacitance of the capacitor and a predetermined resistance.

3. The method of claim 2 further comprising:

periodically inducing the change in the current flowing through the capacitor with a period of greater than ten time constants.

4. The method of claim 1 further comprising:

calculating an ideal value equal to the leakage value offset by approximately 20 percent of a difference between the initial value and the leakage value in response to determining the plurality of current values; and where the intermediate value is selected to be approximately equal to the ideal value in response to calculating the ideal value.

5. The method of claim 1 further comprising:

calculating a range of interest between the leakage value offset by approximately 15 percent of a difference between the initial value and the leakage value and the leakage value offset by approximately 28 percent of the difference between the initial value and the leakage value in response to determining the plurality of current values; and where the intermediate value is selected to be within the range of interest in response to determining the range of interest.

6. The method of claim 1 further comprising:

providing a liquid within the capacitor prior to inducing the change in the current in the capacitor; and calculating a dielectric value of the liquid based upon the capacitance and a known geometry of the capacitor in response to calculating the capacitance.

7. The method of claim 6 further comprising:

calculating a conductivity of the liquid based on the geometry of the sensor, the leakage value, and a strength of an electric field applied across the fluid.

8. The method of claim 1 further comprising:

providing a liquid within the capacitor prior to inducing the change in the current in the capacitor; and calculating a dielectric dissipation factor for the liquid based upon the initial value and the leakage value in response to determining the plurality of current values.

9. The method of claim 1 further comprising:

providing a liquid within the capacitor prior to inducing the change in the current in the capacitor;

controlling a temperature for the liquid to approximately 100 degrees Celsius prior to determining the leakage value;

changing the temperature of the liquid to approximately 40 degrees Celsius in response to determining the leakage value at 100 degrees Celsius;

determining a second leakage value in response to changing the temperature of the liquid; and calculating a viscosity ratio of the liquid based upon the leakage value and the second leakage value.

10. A system for measuring a capacitance of a capacitor, the system comprising:

a resistor connected to the capacitor;

a variable source operational to induce a change in a current through the capacitor;

a sensor operational to convert a current flowing through the resistor into a current value; and a processor operational to record a plurality of current values, the plurality of current values including a initial value and a leakage value determined while the current is approximately steady state, select an intermediate value from the plurality of current values, and calculate the capacitance of the capacitor based upon the initial value, the leakage value, the intermediate value, and a time between inducing the change in the current flowing through the resistor and determining the intermediate value in response to selecting the intermediate value.

11. The system of claim 10 wherein the processor is further operational to delay at least five time constants after the variable source induces the change in the current flowing through the capacitor to determine the leakage current, where one time constant is defined as a product of a predetermined capacitance of the capacitor and a predetermined resistance of the resistor.

12. The system of claim 11 where the variable source is further operational to periodically induce the change in the current flowing through the capacitor with a period of at least ten time constants.

13. The system of claim 10 where the processor is further operational to calculate an ideal value equal to the leakage value offset by approximately 20 percent of a difference between the initial value and the leakage value in response to determining the plurality of current values, and select the intermediate value to be approximately equal to the ideal value.

14. The system of claim 10 where the processor is further operational to calculate a range of interest between the leakage value offset by approximately 15 percent of a difference between the initial value and the leakage value and the leakage value offset by approximately 28 percent of the difference between the initial value and the leakage value, and select the intermediate value to be within the range of interest in response to determining the range of interest.

15. The system of claim 10 having a liquid disposed within the capacitor, and where the processor is further operational to calculate a dielectric value of the liquid based upon the capacitance and a known geometry of the capacitor.

16. The system of claim 15 where the processor is further operational to calculate a conductivity of the liquid based on the geometry of the sensor, the leakage value, and a strength of an electric field applied across the fluid.

17. The system of claim 10 having a liquid disposed within the capacitor, and where the processor is further operational to calculate a dielectric dissipation factor for the liquid based upon the initial value and the leakage value.

18. The system of claim 10 having a liquid disposed within the capacitor, the system further comprising:
    a temperature sensor for converting a temperature of the fluid to a temperature value; and
    the processor being further operational to calculate a viscosity ratio for the fluid based upon a change in the leakage value induced by a change in the temperature of the fluid between approximately 40 degrees and 100 degrees Celsius.

\* \* \* \* \*